US012778461B2

(12) United States Patent
Del Favero et al.

(10) Patent No.: US 12,778,461 B2
(45) Date of Patent: Nov. 3, 2026

(54) NONPARAMETRIC GLUCOSE PREDICTORS

(71) Applicant: Dexcom, Inc., San Diego, CA (US)

(72) Inventors: Simone Del Favero, Valle di Cadore (IT); Andrea Facchinetti, Trissino (IT); Simone Faccioli, Thiene (IT); Gianluigi Pillonetto, Montebelluna (IT); Giovanni Sparacino, Padua (IT)

(73) Assignee: Dexcom, Inc., San Diego, CA (US)

( * ) Notice: Subject to any disclaimer, the term of this patent is extended or adjusted under 35 U.S.C. 154(b) by 964 days.

(21) Appl. No.: 17/645,715

(22) Filed: Dec. 22, 2021

(65) Prior Publication Data

US 2022/0202323 A1 Jun. 30, 2022

Related U.S. Application Data

(60) Provisional application No. 63/129,952, filed on Dec. 23, 2020.

(51) Int. Cl.
*G01N 33/66* (2006.01)
*A61B 5/145* (2006.01)
*G16H 50/50* (2018.01)

(52) U.S. Cl.
CPC ......... *A61B 5/14532* (2013.01); *G01N 33/66* (2013.01)

(58) Field of Classification Search
None
See application file for complete search history.

(56) References Cited

U.S. PATENT DOCUMENTS

2011/0196213 A1* 8/2011 Thukral ............... A61B 5/7275 600/301
2011/0237917 A1* 9/2011 Roy ..................... A61B 5/1495 702/19

(Continued)

FOREIGN PATENT DOCUMENTS

EP 4268242 B1 12/2025
JP 2008545489 A 12/2008

(Continued)

OTHER PUBLICATIONS

Wang Q, Molenaar P, Harsh S, et al. Personalized State-space Modeling of Glucose Dynamics for Type 1 Diabetes Using Continuously Monitored Glucose, Insulin Dose, and Meal Intake: An Extended Kalman Filter Approach. Journal of Diabetes Science and Technology. 2014;8(2):331-345. (Year: 2014).*

(Continued)

*Primary Examiner* — Adam J Eiseman
*Assistant Examiner* — Nelson Alexander Glover
(74) *Attorney, Agent, or Firm* — Patterson and Sheridan, LLP

(57) ABSTRACT

A method of predicting future blood glucose concentrations of an individual patient includes: identifying an individualized linear black box model of glucose-insulin by estimating (Continued)

*Example of input signals, before (a) and after (b) input transformation* a plurality of impulse response functions each accounting for an input-output relation of a plurality of individualized patient data sets, the impulse response functions being functions in a Reproducing Kernel Hilbert Space (RKHS); and applying a linear predicting technique to the selected model using the identified impulse response functions to obtain a predicted blood glucose concentration of the individual patient at a future time.

11 Claims, 5 Drawing Sheets

(56) References Cited

U.S. PATENT DOCUMENTS

| | | | | |
|---|---|---|---|---|
| 2013/0231543 | A1* | 9/2013 | Facchinetti | A61B 5/746<br>600/365 |
| 2014/0073892 | A1* | 3/2014 | Randloev | G16H 50/50<br>600/365 |
| 2018/0027412 | A1* | 1/2018 | Mandapaka | H04W 12/069<br>713/151 |
| 2018/0317817 | A1* | 11/2018 | Jos | A61B 5/7275 |

FOREIGN PATENT DOCUMENTS

| | | | |
|---|---|---|---|
| JP | 2017527421 | A | 9/2017 |
| WO | 2006132899 | A2 | 12/2006 |

OTHER PUBLICATIONS

Chuiso et al. System Identification: A Machine Learning Perspective: Annual Reviews (Year: 2019).*

Favero S.D., et al., "A Novel Nonparametric Approach for the Identification of the Glucose-insulin System in Type 1 Diabetic Patients," Preprints of the 18th IFAC World Congress Milano (Italy) Aug. 28-Sep. 2, 2011, Jan. 1, 2011, Retrieved from the Internet:URL:https://folk.ntnu.no/skoge/prost/proceedings/ifac11-proceedings/data/html/papers/1929.pdf on Oct. 28, 2011, pp. 8340-8346.

International Search Report and Written Opinion for Application No. PCT/US2021/073093, mailed Apr. 22, 2022, 15 pages.

Messori M., et al., "Model Individualization for Artificial Pancreas," Computer Methods Programs Biomedicine, vol. 171, Apr. 1, 2019, pp. 133-140.

Del Favero S., et al., "A Novel Nonparametric Approach for the Identification of the Glucose-Insulin System in Type 1 Diabetic Patients," IFAC Proceedings vols. 2011, pp. 8340-8346.

* cited by examiner

*Example of input signals, before (a) and after (b) input transformation*

*Comparison of log(CondNum) using input transformation (input transf) or not (state-of-art mean scale), for a parametric (P) or a non-parametric (NP) identification technique*

*Training data after preprocessing of the subject #1*

*PH = 30 min*

*PH = 60 min*

*PH = 90 min*

*PH = 120 min*

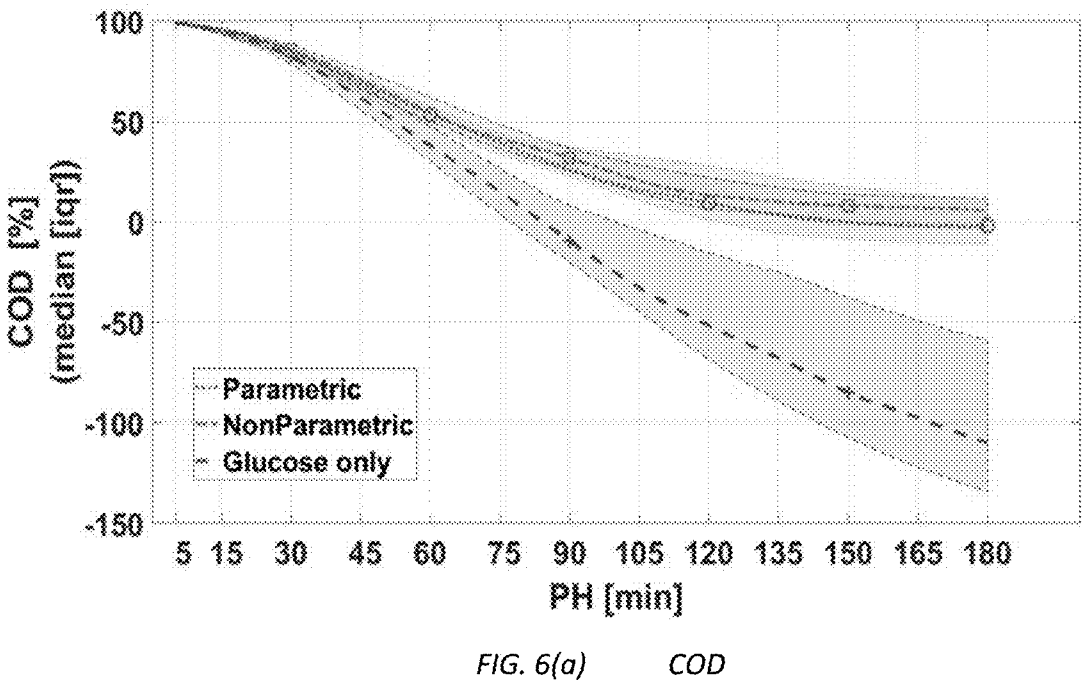
FIG. 6(a) COD
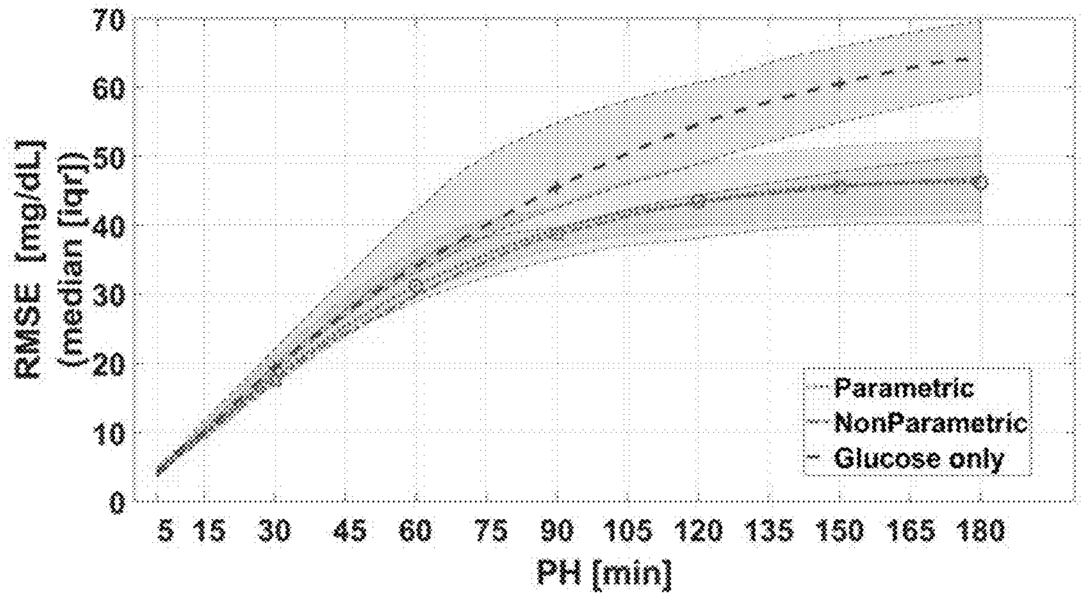
FIG. 6(b) RMSE

NONPARAMETRIC GLUCOSE PREDICTORS

CROSS-REFERENCE TO RELATED APPLICATIONS

This application claims the benefit of U.S. Provisional Application No. 63/129,952, filed Dec. 23, 2020, the entire contents of which are incorporated by reference herein.

BACKGROUND

The autoimmune metabolic disease called type-1 diabetes (T1D) is characterized by the destruction of the pancreatic beta-cells, responsible for insulin production. The consequent inability to produce insulin, a crucial hormone in glucose homeostasis, is associated with anomalous blood glucose (BG) levels in the body. To keep BG in a safe range, T1D patients need to administer themselves insulin through external infusions. High glucose levels in the body, which could lead to several complications on the long term, can be caused by insufficient insulin administration. Conversely, hypoglycemia (BG less than 70 mg/dL) represents an immediate threat for subject's life, and it can be caused by an insulin over-treatment.

T1D management can be considerably improved by accurate predictions of future glucose levels, and by the design of specific alarm systems through which upcoming critical situations can be detected and prevented. Another promising advancement in T1D management is the so-called artificial pancreas (AP), a system that uses closed-loop control (CLC) algorithms to automatically modulate the insulin infusion, and references therein: several control algorithms for AP leverage predictive models, including the model predictive control (MPC).

The key component of both predictive alert systems and AP is the mathematical model used to describe glucose dynamics, which must be able to deal with inter- and intra-subject variability: the glucose response to insulin and meal is different in every person, and even in the same patient changes over time. This issue can be addressed by learning and updating patient-specific models of the glucose-insulin dynamics and using them to design individualized predictive alert algorithms, or to personalize the model-based CLC algorithm of an AP system.

SUMMARY

In one aspect, systems and methods are described herein that use black-box model-learning algorithms to produce a description of a patient-specific glucose-insulin system that could be integrated, for example, into glucose prediction and control algorithms. In some embodiments a linear time-invariant model is employed. The selection of such a model has a number of advantages. First, for this class of models, the parameters estimation algorithms have been deeply studied in the literature, making available powerful convergence results and statistical properties analysis. Second, these models can be used to generate predictions simply by resorting to well-established and computationally convenient techniques such as the Kalman filter. Third, they are well suited for model-based control schemes such as model predictive control MPC), providing computationally parsimonious implementation. Finally, although the metabolic physiology is non-linear, various experiments (both in-silico and in-vivo) indicate that a linear approximation may suffice to capture the dynamic features essential for a successful control design.

Besides classical parametric models (ARX, ARMAX, ARIMAX, Box-Jenkins) identified using the prediction error method (PEM), in some embodiments a newly emerging paradigm for linear black-box model identification, the non-parametric approach, may be used. This approach has been shown in a preliminary assessment to exhibit superior prediction performance with respect to traditional identification methods on glucose-insulin data in a preliminary assessment.

In yet other embodiments of the systems and techniques described herein, the various degrees of freedom available in the parametric approaches may be used to assess their impact. In particular, a comparison is made between various system parametrizations, various model-order selection criteria, and different parameters estimation methods. The assessment of the various model-learning techniques is performed employing a large experimental dataset collected on a population of 11 T1D individuals using an AP system 24/7 for 5 months. The results show that in some cases non-parametric linear model-learning provides a statistically significant improvement with respect to the parametric approach.

In one particular aspect, a method of predicting future blood glucose concentrations of an individual patient is provided. The method includes: identifying an individualized linear black box model of glucose-insulin by estimating a plurality of impulse response functions each accounting for an input-output relation of a plurality of individualized patient data sets, the impulse response functions being functions in a Reproducing Kernel Hilbert Space (RKHS); and applying a linear predicting technique to the selected model using the identified impulse response functions to obtain a predicted blood glucose concentration of the individual patient at a future time.

In an embodiment of this particular aspect, the linear predicting technique is a Kalman filter.

In another embodiment of this particular aspect, the individualized linear black box model is a time-invariant model.

In another embodiment of this particular aspect, the plurality of individualized input patent data sets includes a data set of previous glucose levels over time for the individual patient, a meal intake data for the individual patient and exogenous insulin delivered to the individual patient over time.

In another embodiment of this particular aspect, 5 preprocessing of the meal intake data and the exogenous insulin that is delivered is performed to decouple the meal intake data from the exogenous insulin that is delivered so that the meal intake data and the exogenous insulin that is delivered are not linearly dependent on one another.

In another embodiment of this particular aspect, the data set of previous glucose levels over time for the individual patient is provided by a continuous glucose monitor.

In another embodiment of this particular aspect, a Stable-Spline Kernel is selected for a kernel of the RKHS.

In another embodiment of this particular aspect, kernel hyperparameters are estimated using maximum marginal likelihood or cross-validation.

BRIEF DESCRIPTION OF THE DRAWINGS

FIGS. 6*a* and 6*b* show the COD metric and the root mean squared error (RMSE) metric, respectively, comparing the performance achieved by a CGM-only model, a parametric model identified using insulin and meal data and a non-parametric model with inputs

DETAILED DESCRIPTION

I. Introduction

Several different glucose-insulin models have been proposed in the literature. According to a high-level classification, these models can be divided in white-box vs. black-box. White-box models are based on mechanistic/semimechanistic description of the physiological processes undergoing in the metabolic system. Their complexity, i.e., number of equations and model parameters, varies greatly depending on the model purpose: "minimal models", are parsimonious approximate descriptions designed to ensure parameters identifiability in special experimental conditions (e.g., oral glucose tolerance test), while "maximal models" are large-scale models with several equations and parameters mainly designed for simulating in-silico trials. Both minimal and maximal physiological models present some issues when used for model-based glucose prediction or model-based control: minimal models are often too rigid to provide adequate data prediction, while maximal models are normally hard to identify and, hence, present limited effectiveness in dealing with intra- and inter-patient variability. Furthermore, physiological models are non-linear, making the model-based computation of predictions and their use in control algorithms non-trivial, often resulting in computationally expensive algorithms. For these reasons, large efforts have been concentrated in exploring black-box models, which do not describe any physiological process and are simply data driven. In the glucose mathematical modeling literature, several data-driven approaches have been proposed so far, either using classical linear models derived with system identification methods, or with non-linear models obtained using machine learning (ML) strategies or deep learning (DL) techniques. Despite several options having been considered, no algorithm has clearly and significantly outperformed the others in terms of prediction accuracy.

Figure 1:
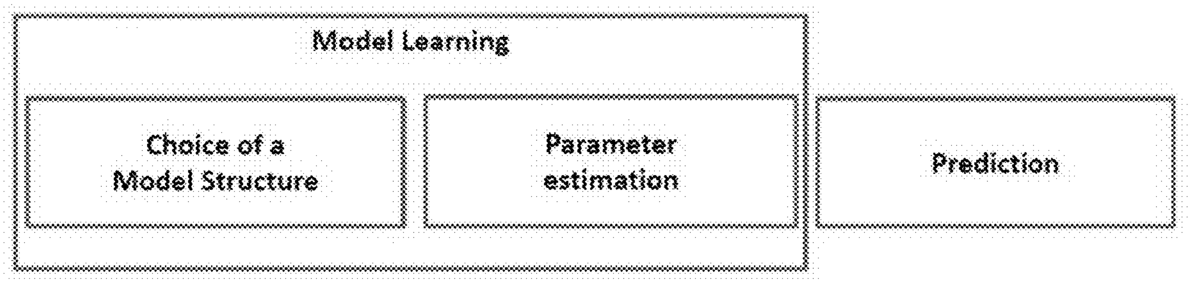
FIG. 1 is flowchart illustrating at a high level the steps involved in the individualized model-based prediction scheme described herein.

FIG. 1 is flowchart illustrating at a high level the steps involved in the individualized model-based prediction scheme described herein. As shown, the first step 10 in the scheme selects a suitable model structure from among the various available options described above. In the present case the selected model is an individualized linear black-box model of glucose-insulin regulation. As described below, the selected model has model parameters that can be individualized from easily accessible patient logs, such as carbohydrate intake and insulin infusion data, to mimic an individual specific physiology.

In the second step 20 of the prediction scheme shown in FIG. 1 selected ones of the model parameters that are to be personalized for an individual patient are estimated using a nonparametric estimation technique. In one embodiment the parameter estimation technique that is used employs a support vector regression approach, a Gaussian regression approach and a Tikhonov regularization approach. Next, in the third step 30 the obtained personalized model is used within a prediction scheme based, for example, on a linear prediction scheme such as a Kalman filter.

II. Experimental Data

A. Experimental Arrangement

Data were collected during a multicenter clinical trial (www.clinicaltrials.gov: NCT02137512) aimed to assess the feasibility of a long-term closed-loop control (CLC) algorithm within an automated insulin delivery system, namely the Diabetes Assistant (DiAs) developed at the University of Virginia. The study and all experimental procedures were approved by each Institutional or Independent Review Boards, and were overseen by independent Data and Safety Monitoring Boards. Fourteen individuals affected by T1D participated to a 5-month trial testing 24/7 the use of the DiAs system. Glucose data were recorded using a DexCom G4 sensor (DexCom, Inc., San Diego, CA, USA) with a sample time of 5 min, whereas insulin was infused with a Roche Accu-Check Spirit Combo insulin pump (Roche Diabetes Care, Inc., Indianapolis, IN, USA). These two off-the-shelf diabetes devices used low energy Bluetooth to communicate with the principal system component, a platform based on an Android smartphone.

Additional details concerning the data may be found in B. Kovatchev et al., "Feasibility of Long-Term Closed-Loop Control: A Multicenter 6-Month Trial of 24/7 Automated Insulin Delivery," Diabetes Technology and Therapeutics, vol. 19, no. 1, pp. 18-24, 2017. For present purposes a few details concerning the T1D patient therapy are highlighted below and a suitable notation is introduced.

Individuals were instructed to manually deliver a proper amount of insulin for all meals, by inserting in the system all carbohydrate (CHO) intake. We will refer to this manually recorded signal as "meal signal", m(k). As far as insulin is concerned, at every time step k, the system injected an insulin dose i(k) that can be seen as the sum of two components:

$$i(k) = i_{ST}(k) + \Delta i_{CL}(k),$$

where $i_{ST}(k)$ is the insulin prescribed by the standard T1D therapy for patients not using an AP system, and $\Delta i_{CL}(k)$ is the real-time insulin correction computed by the CLC algorithm. The insulin $i_{ST}(k)$ can be further decomposed as $i_{ST}(k)=I_b+i_B(k)$, where $I_b$ is the amount of insulin that should be injected in order to maintain BG stable during fasting periods (known as basal insulin, a piece-wise constant signal), while $i_B$ (k) is the insulin administered at meal-time to mitigate postprandial peak (known as meal bolus). Specifically, at meal time:

$$\begin{aligned} i_{ST}(k) &= I_b + i_B(k) \\ &= I_b + \underbrace{\frac{m(k)}{ICR}}_{i_M(k)} + \underbrace{\frac{g(k) - G_{target}}{CF} - iob(k)}_{i_{Corr}(k)} \end{aligned} \quad (2)$$

where m(k) is the estimated amount of CHO to be consumed, g(k) the recorded glucose level, and $G_{target}$ the BG target. ICR and CF are known as insulin-to-carbohydrate ratio and correction factor, respectively. These two patient-specific numbers, suggested by a clinician, refer to how much insulin is needed to cover a specific amount of carbohydrates, and how much insulin is needed to lower the BG by 1 mg/dL, respectively. Finally, the insulin on board, iob(k), refers to how much insulin from recently delivered boluses is still present in the body.

Note that $i_M$ (k) is known as meal-centric bolus component, and aims to provide the insulin coverage of the ingested CHO, while the remaining part, $i_{Corr}$(k), is the so-called corrective component, that contains a manual insulin correction to compensate for high-glucose levels at meal time, or to take into account of still working insulin in the body.

B. Data Preprocessing

In this section, we illustrate the preprocessing steps performed on the trial data and aimed at obtaining three signals equally sampled at $T_S$=5 min without missing values, describing insulin-related information, i(k), carbohydrates intake, m(k), and CGM measured glucose, g(k).

Glucose and insulin data were collected from different devices, while meals were manually logged by the subjects: the related time series were thus slightly unsynchronized and contained missing values.

To enforce synchronization, all signals were aligned to the same time grid. Then, we considered the missing data. First, patients which had more than 20% of missing data were discarded, resulting in the exclusion of two subjects. On the remaining data, incomplete data portions lasting more than 30 min were discarded, while shorter gaps were interpolated. The interpolation strategy depends on whether the gap occurred in training or test data, as discussed in the following. Finally, a data portion of 14 consecutive days was searched and found in the remaining patients except for one, resulting in a total of three excluded subjects.

For each of the 11 retained subjects, the previously identified 14-day data portion was split in two parts: the first 7 days were used for model training (training-set) while the subsequent 7 days to assess the prediction performance (test-set) on independent data.

Figures 2A, 2B:
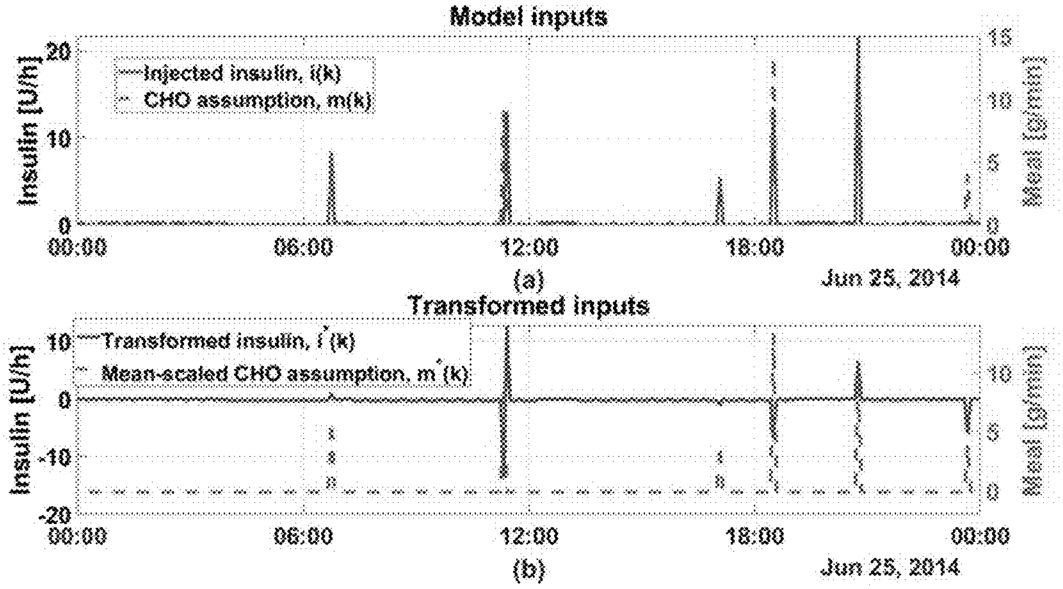
FIGS. 2*a* and 2*b* show insulin input data signals before and after being transformed to reduce collinearity, respectively.

The insulin i(k) and meal m(k) signals, both available in our arrangement, strongly affect BG level g(k). For this reason, we consider them as input to a model having glucose g(k) as output. Furthermore, their physiological impact on glucose is very different: insulin injections decrease BG while CHO assumptions increase it. This suggests that these two signals convey very different information and therefore it is important to have both of them as inputs for accurate prediction of future BG levels. However, these two inputs are very similar to one another, as illustrated in FIG. 2*a*, since every CHO consumption is associated to an insulin bolus, dominated by the meal-centric component (see equation 2) and thus almost linearly proportional to m(k). Intuitively, it is clear how this poses a major challenge for black-box model-learning approaches: in the training data there are only instances where both signals increase simultaneously, making it difficult for the model-learning method to infer from the data the role of each input without any physiological prior information. This fact was previously noticed and reported in relation to linear models. In statistical learning and system identification this phenomenon is a known problem called input collinearity. More specifically, a crucial step in several identification procedures is the inversion of a matrix D built from the training data, that in our case will contain insulin and meal values: the computation of the inverse of a matrix containing collinear signals is prone to large numerical errors. Collinearity can be quantified by the condition number of this matrix, CondNum (D), an index that measures how sensitive a function is to changes or errors in the input, and in our case it can be used as a diagnostic for collinearity.

The condition number of D is defined as $$CondNum(D) = \frac{\sigma_{max}(D)}{\sigma_{min}(D)},$$

where $\sigma_{max}$(D) and $\sigma_{min}$(D) are, respectively, the maximum and minimum singular values of D. If the condition number is at most slightly larger than one, the matrix is well-conditioned, which means that its inverse can be computed with good accuracy. If the condition number is very large, then the matrix is said to be ill-conditioned: practically, such a matrix is almost singular, and the computation of its inverse is prone to large numerical errors. A matrix that is not invertible has condition number equal to infinity.

In our case, with the collinearity of inputs we can have an ill-conditioned matrix: this can lead to a very large CondNum, and hence to a low accurate matrix inversion. To address this issue, in some embodiments an input transformation may be used to mitigate the collinearity, which decouples the two input signals while keeping their interpretability. The new signals are defined as:

$$i^*(k) = i(k) - \left(I_b + \frac{m(k)}{ICR}\right),$$

$$m^*(k) = m(k) - \bar{m},$$

where $\overline{m}$ is the sample mean of the signal m(k) computed on the training set. In this way, the transformed insulin signal, i*(k), contains only the information that is not strictly related to a carbohydrate assumption (see FIG. 2*b*): the corrective component of the insulin bolus, $i_{Corr}$(k), and the real-time insulin correction computed by the CLC algorithm, $\Delta i_{CL}$(k).

Figure 3:
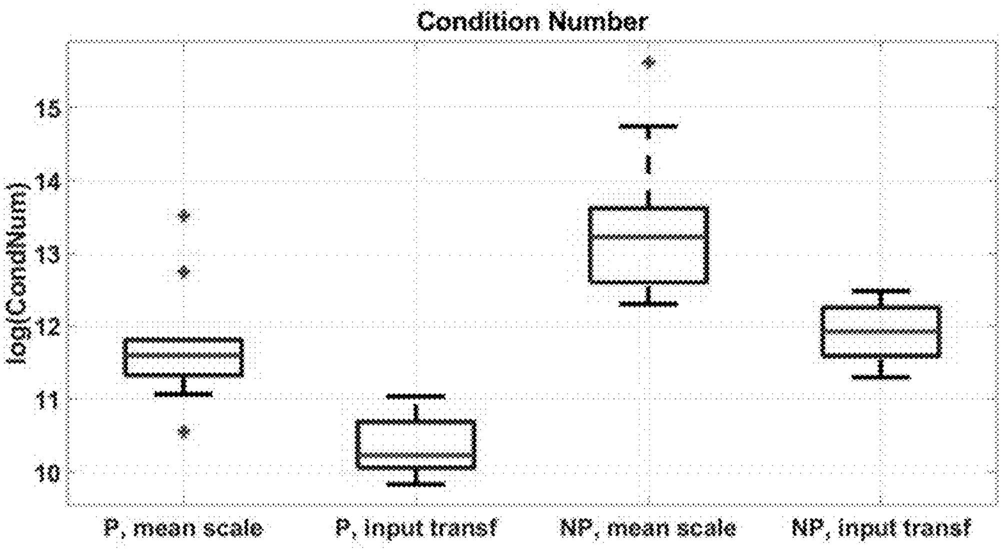
FIG. 3 shows the CondNum index (a diagnostic for collinearity) of the training-set matrix that needs to be inverted for model identification for four different cases.

The proposed transformation results in a significant reduction in the condition number of the matrices to be inverted in parametric and non-parametric identification algorithms, thus proving its efficacy in reducing collinearity. FIG. 3 shows the CondNum of the training-set matrix that need to be inverted for model identification, in 4 different cases: using the new input transformation (input transf) or not (state-of-art mean scale), with a parametric (P) or a non-parametric (NP) identification technique. As we can see, the input transformation significantly lowers the CondNum, leading to a more well-conditioned inversion problem: we obtained an improvement of about 80% and 87% with, respectively, the parametric and the non-parametric approach.

Once again for numerical stability reasons, it is important that the units of measurement are chosen so that signals values span similar ranges. In our case, this is done using [g/min] and [U/h] for meal and insulin information, respectively, while CGM readings are expressed in [mg/dL]. Finally, as per standard system identification pipeline, the glucose g(k) signal is processed by mean scaling, i.e. removing an estimate of its mean:

$$g^*(k) = g(k) - \bar{g}.$$

with $\bar{g}$ being the sample mean computed on the training-set.

Figure 4:
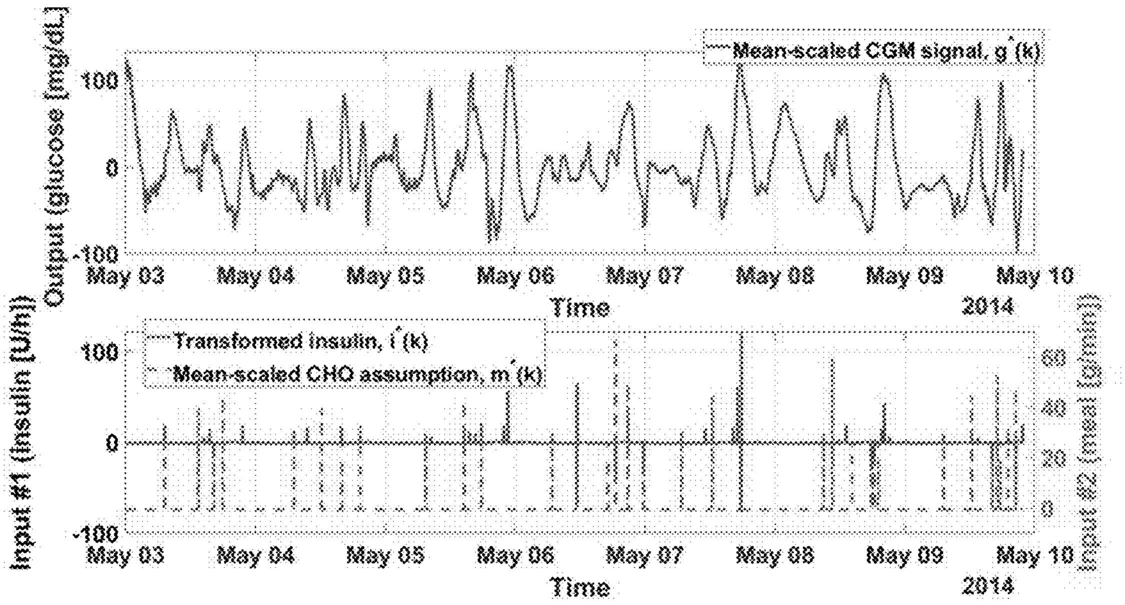
FIG. 4 shows an example of input training data after undergoing preprocessing.
Figure 5A:
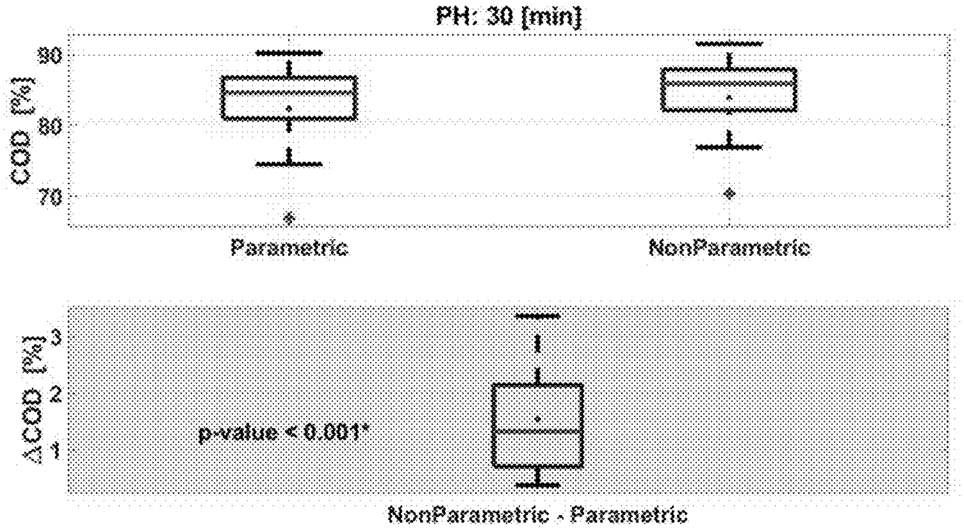
FIGS. 5*a*-5*d* show a coefficient of determination metric (COD) to compare a parametric model vs. a non-parametric model for four different prediction horizons.
Figure 5B:
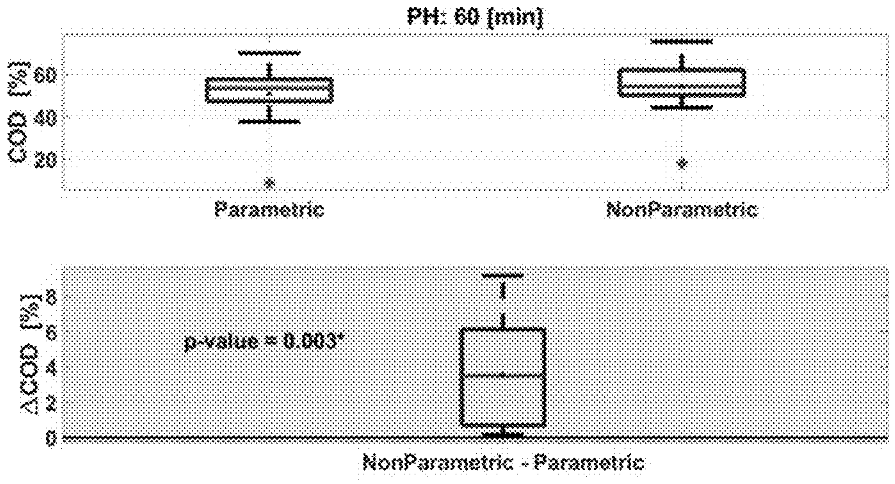
Figure 5C:
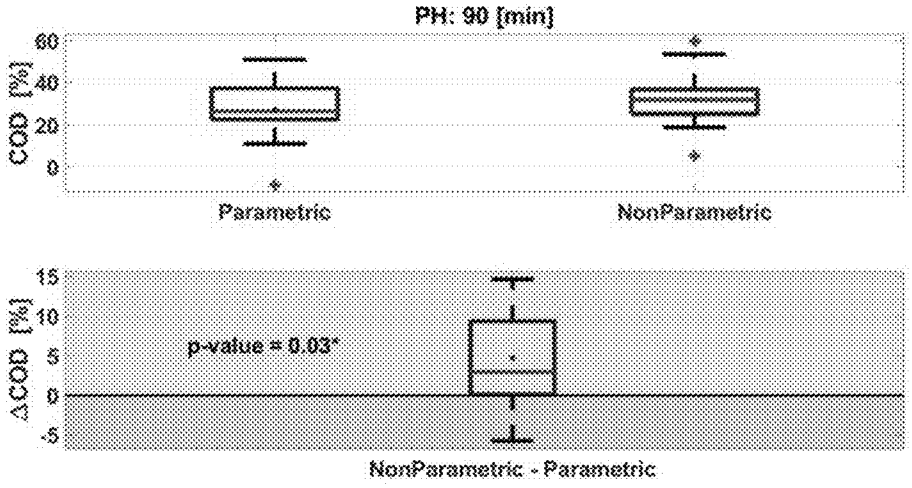
Figure 5D:
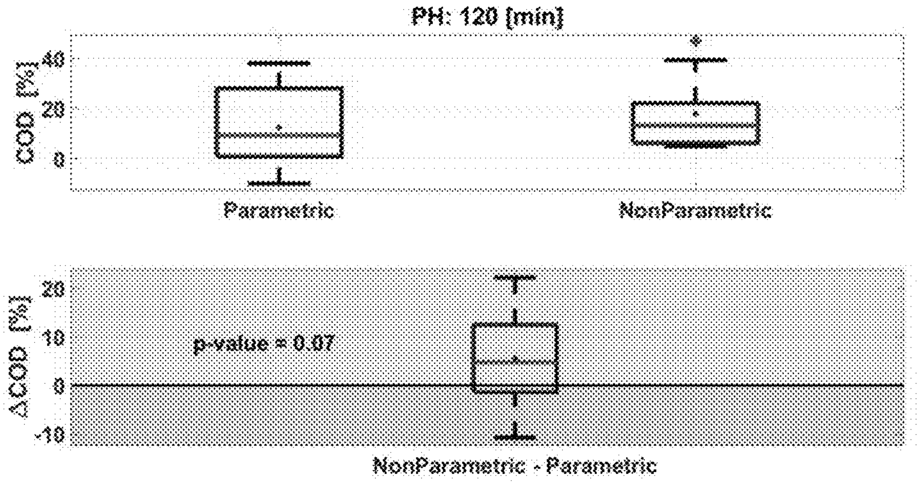

To avoid a cumbersome notation, in the following we will denote the preprocessed data used in the identification process simply as g(k), i(k), and m(k), dropping the *. Finally, FIG. 4 shows an example of data, specifically the training-set used for the identification of the subject #1 after the abovementioned preprocessing steps.

The entire training-set is available during model training, that we envision retrospectively performed on previously collected patient data. On the other hand, glucose prediction should be performed in real-time. As a consequence, not all the test-set should be considered known when predicting glucose at time k. In particular, the sample mean of inputs and output computed on the entire test-set cannot be used as a real-time preprocessing. Instead, in the above preprocessing we subtract both training and test data the mean values of the signals computed on the training-set.

Similarly, third-order spline interpolation was used to fill data gaps of less than 30 minutes in the training-set but, since this technique is non-causal, it cannot be used in the test-set. Instead, zero-order hold was used on test data as it is applicable in real-time.

III. Identification Techniques

As anticipated above, one aspect of the systems and techniques described herein identifies linear time-invariant black-box Multi-Input-Single-Output (MISO) models that have as inputs the (transformed) insulin i(k) and meal information m(k), and as output the glucose level g(k). This amounts to identify system transfer function or, equivalently, the system impulse response. To do so, two different approaches are considered: parametric and non-parametric strategies.

A. Parametric Approach

The parametric approach restricts the search of the system dynamics to a finite-dimensional set of transfer functions parametrized by a parameters vector:

$$g(k) = G_1(z^{-1}, \theta)\ i(k-n_{k1}) + G_2(z^{-1}, \theta)\ m(k-n_{k2}) + H(z^{-1}, \theta)\ e(k), \quad (5)$$

where $G_1(z^{-1}, \theta)$ and $G_2(z^{-1}, \theta)$ are discrete-time transfer functions parametrized by θ, and where the parameters $n_{k1}$, $n_{k2}$ have been introduced to capture the physiological delays in the inputs action. The output is also corrupted by a colored noise, obtained filtering a white zero-mean noise e(k) through the transfer function $H(z^{-1},\theta)$. Commonly used parametrization are auto regressive with exogenous input (ARX), auto regressive moving average with exogenous input (ARMAX), auto regressive integrated moving average with exogenous input (ARIMAX), and Box-Jenkins (BJ), listed in increasing order of generality.

The first degree of freedom in the parametric identification pipeline is therefore the choice of a suitable model class: in this work we considered all the above listed options. Another choice that has to be addressed in the identification pipeline is the model complexity, i.e., the number of parameters that have to be estimated (model order). Details on this step are described below.

Finally, the model parameters have to be estimated: the state-of-art approach is the prediction error method (PEM), where the parameter vector is found so as to minimize the 1-step ahead prediction error committed by the associated predictor $\hat{g}(k|k-1,\theta)$. However, in this work we also considered the option of minimizing the prediction error at other prediction horizon (PH):

$$\hat{\theta}_{PH} = \underset{\theta}{\operatorname{argmin}} \frac{1}{N} \sum_{1}^{N} (g(k) - \hat{g}(k \mid k-PH, \theta))^2$$

where PH is a generic prediction horizon, $\hat{g}(k|k-PH,\theta)$ is the PH-step ahead predictor parametrized by θ, and N is the number of available data.

Model order selection is performed considering two well-known parsimony criteria, the Akaike Information Criterion (AIC), and the Bayesian Information Criterion (BIC). Moreover, for this task we performed also a 7-fold Cross-Validation (CV): for each round of CV we partitioned seven times the data into complementary subsets: 6 days of data were used to train the model, and the remaining day was used to assess the model performance.

Note that exploring all possible orders combinations would have led to a computationally unfeasible analysis: indeed, preliminary studies on an in-silico population, or on real data, showed that a systematic exploration could lead only to a very little improvement in terms of prediction accuracy. For this reason, we forced all the polynomials orders to be equal. We tested orders ranging from 1 to 20 for ARX, ARMAX and ARIMAX parametrizations, whereas from 1 to 15 using BJ models.

The two delays were fixed to physiological values, i.e., $n_{k1}=9$ step and $n_{k2}=3$ step, corresponding to 45 min and 15 min.

B. Non-Parametric Approach

Let us now consider that the 1-step ahead predictor can be written as:

$$\hat{g}(k \mid k-1, \theta) = h_1 * i(k) + h_2 * m(k) + h_3 * g(k),$$

where * represents the convolution between two signals, whereas $h_1$, $h_2$, and $h_3$ are impulse responses related to the insulin, meal, and glucose signal, respectively. These functions are unknown, and they have to be estimated from noisy measurements. The estimation of these unknown responses can be performed by solving an optimization problem in an infinite-dimensional functional space given by a reproducing kernel Hilbert space (RKHS). The kernel of the RKHS should reflect the properties of the functions to be estimated and its choice is a key point in the non-parametric approaches. Indeed, it can incorporate useful prior knowledge, e.g. smoothness; moreover, the trade-off between data fit and regularity of the estimate can be properly handled by the estimate of the kernel's unknown parameters. In order to incorporate within the kernel the stability of the predictor's impulse responses, in this study we used the Stable-Spline kernel (SSK), proposed in G. Pillonetto, A. Chiuso, and G. De Nicolao, "Predictor estimation via Gaussian regression," *Proceedings of the IEEE Conference on Decision and Control*, pp. 744-749, 2008 and G. Pillonetto and G. De Nicolao, "A new kernel-based approach for linear system identification," *Automatica*, vol. 46, no. 1, pp. 81-93, 2010, which are incorporated by reference herein in their entirety. Using this approach, a generic Stable-Spline impulse response $f_{SSK}$ is seen as a realization of a zero-mean Gaussian random process, whose covariance specify the SSK kernel, and can be written as $$Cov(f_{SSK}(k), f_{SSK}(l)) = \lambda^2 K(k, l) = \lambda^2\left(\frac{e^{-\beta(k+l)}e^{-\beta max(k,l)}}{2} - \frac{e^{-3\beta max(k,l)}}{6}\right)$$

where k,l=1,2, . . . , ∞, β>0, and λ>0. Let now define $K_{h_1}$, $K_{h_2}$, and $K_{h_3}$ as the SSK of $h_1$, $h_2$, and $h_3$ respectively, and let $\mathcal{H}_{h_1}$, $\mathcal{H}_{h_2}$, and $\mathcal{H}_{h_3}$ denote the RKHS of deterministic functions on ℕ associated with $K_{h_1}$, $K_{h_2}$, and $K_{h_3}$ (with norms denoted by $$\|\bullet\|_{\mathcal{H}_{h_1}}, \|\bullet\|_{\mathcal{H}_{h_2}}, \text{ and } \|\bullet\|_{\mathcal{H}_{h_3}}).$$

The Stable-Spline estimators $\hat{h}_1$, $\hat{h}_2$, and $\hat{h}_3$ are obtained from the solution of the following Tikhonov-type problem $$(\hat{h}_1, \hat{h}_2, \hat{h}_3) = \underset{h_1\in\mathcal{H}_{h_1}, h_2\in\mathcal{H}_{h_2}, h_3\in\mathcal{H}_{h_3}}{\operatorname{argmin}} \left\{\|g^+ - Ah_1 - Bh_2 - Ch_3\|^2 + +\gamma_{h_1}\|h_1\|^2_{\mathcal{H}_{h_1}} + \gamma_{h_2}\|h_2\|^2_{\mathcal{H}_{h_2}} + \gamma_{h_3}\|h_3\|^2_{\mathcal{H}_{h_3}}\right\} \quad (9)$$

$$[A]_{kl} = i(k-l),\quad [B]_{kl} = m(k-l),\quad [C]_{kl} = g(k-l)$$

$$k = 1, 2, \ldots, \infty,\quad l = 1, 2, \ldots, n$$

$$g^+ = [g_1\ g_2\ \ldots\ g_n]^T$$

where ||•|| is the Euclidian norm, $$\gamma_{h_1} = \sigma^2/\lambda^2_{h_1}, \gamma_{h_2} = \sigma^2/\lambda^2_{h_2}, \gamma_{h_3} = \sigma^2/\lambda^2_{h_3},$$

and $g^+$ is a vector containing n CGM data with n being the number of future samples considered in the identification procedure. Note that, to make practically implementable the above strategy, the infinitely long impulse responses are approximated by truncation after $N_{pred}$ samples.

Note also that from (equation 12) the covariances of the impulse responses $h_1$, $h_2$, and $h_3$ include the parameters $\beta_{h_1}$, $\beta_{h_2}$, and $\beta_{h_3}$, respectively. We can therefore define the hyperparameters of our problem ($\beta_{h_1}$, $\beta_{h_2}$, $\beta_{h_3}$, $\lambda_{h_1}$, $\lambda_{h_2}$, $\lambda_{h_3}$, and σ), that have to be properly tuned before to the solution of the Tikhonov problem (equation 13). By assuming known the hyperparameters, the solution of (equation 13) is given by $$\hat{h}_1 = \lambda^2_{h_1} K_{h_1} A^T \phi,$$

$$\hat{h}_2 = \lambda^2_{h_2} K_{h_2} B^T \phi,$$

$$\hat{h}_3 = \lambda^2_{h_3} K_{h_3} C^T \phi,$$

$$\phi = (\lambda^2_{h_1} A K_{h_1} A^T + \lambda^2_{h_2} B K_{h_2} B^T + +\lambda^2_{h_3} C K_{h_3} C^T + \sigma^2 I_n)^{-1} g^+,$$

where $I_n$ is the n×n identity matrix.

Regarding the hyperparameters (denoted by ζ), we estimated them via maximum marginal likelihood:

$$\hat{\zeta} = \underset{\zeta}{\operatorname{argmin}}(J(g^+, \zeta)),$$

$$J(g^+, \zeta) = \frac{1}{2}\ln(\det[2\pi V[g^+]]) + \frac{1}{2}(g^+)^T (V[g^+])^{-1} g^+,$$

$$V[g^+] = \lambda^2_{h_1} A K_{h_1} A^T + \lambda^2_{h_2} B K_{h_2} B^T + +\lambda^2_{h_3} C K_{h_3} C^T + \sigma^2 I_n,$$

where J is the opposite log-marginal likelihood of $g^+$.

Let us now make a parallelism with the state-of-art parametric approach. The choice of the kernel might be seen as the logical counterpart of the model's class selection. Whereas the estimation of the kernel hyperparameters can be seen as the counterpart of the model-order selection and can be performed by well-established criteria such as maximum marginal likelihood or cross validation. The major advantage of kernel-based identification is its flexibility: on one side, the parametric model selection forced the choice of a finite and integer number of parameters; whereas, on the other side, the non-parametric strategy uses a fine tuning of regularization parameters by means of well-established criteria. In addition, the SSK contains only two unknown parameters, namely the variance of the impulse response at time zero and its decay rate to zero. Therefore, it is only required to solve a non-linear optimization problem in a low-dimensional space (2 hyperparameters for each of the 3 impulse responses).

The non-parametric approach was implemented in two different ways. On one hand, we considered the Matlab built-in function. This option treats the problem as a regularized parametric approach, considering models of very high order and adding to the standard PEM cost function a regularization term representing a suitable prior on the unknown coefficients, so that overfitting is avoided. As a suitable prior, we adopted the Stable-Spline kernel. On the other hand, we implemented ad-hoc all the passages we have just presented.

IV. Evaluation Metrics

To assess the prediction accuracy of the identified models, we compared the prediction of future CGM values against its actual measured value. Different prediction horizons (PH) were considered.

Let us denote with ĝ(k|k−PH) the PH-step ahead prediction of a model, i.e., the prediction obtained by using past glucose values up to time k−PH, g(k−PH), g(k−PH−1), . . . , and inputs up to time k, i(k), i(k−1), . . . , m(k), m(k−1), . . . The two signals, g(k) and ĝ(k|k−PH), were compared using three different metrics, namely root mean squared error (RMSE), coefficient of determination (COD), and time gain (TG), commonly used in system identification.

$$RMSE(PH) = \frac{1}{\sqrt{N}}\|g(k) - \hat{g}(k \mid k - PH)\|_2$$

where $\|x(k)\|_2$ denotes the $\ell_2$ norm of the signal x(k), namely $$\sqrt{\sum_1^N x(k)^2},$$

N being the number of samples in the trace.

The metric COD is defined as $$COD(PH) = 100\left(1 - \frac{\|g(k) - \hat{g}(k \mid k - PH)\|_2^2}{\|g(k) - \bar{g}\|_2^2}\right)$$

where $\bar{g}$ is the sample mean of the glucose signal. COD is based on the ratio between the mean squared prediction error (MSE)

$$\|g(k) - \hat{g}(k \mid k - PH)\|_2^2,$$

i.e., the sample variance of the prediction error, and the sample variance of the signal $$\|g(k) - \bar{g}\|_2^2.$$

This normalization accounts for the fact that signals with larger variance are expected to produce larger prediction errors. When RMSE=0 then COD achieves its maximum possible value, COD=100%; when the RMSE equals the signal sample variance then COD=0%; if the norm of the error increases further, COD becomes negative.

Furthermore, we considered the time gain (TG) granted by the prediction as $$TG(PH) = PH - \text{delay}(PH),$$

where the delay between the original and the predicted profiles is quantified by the temporal shift τ that maximizes the cross-correlation (crossCorr), a measure of similarity between g and a shifted version of ĝ:

$$\text{delay}(PH) = \frac{\text{argmax}}{\tau} crossCorrg(k), \hat{g}(k \mid k - PH)^{\tau} \quad (15)$$

The higher the TG, the more useful the prediction.

To compare the accuracy metrics among different complexity criteria an analysis of variance (ANOVA) was performed. The Kruskal-Wallis test was used in place of the ANOVA when one of the analyzed distributions was found non-normal by a Lilliefors test. A paired t-test was performed to compare parametric vs. non-parametric models.

All p-values reported are two-tailed and considered statistically significant when <0.05.

V. Results

Starting from the parametric approach, the first degree of freedom assessed is the choice of the model order. The prediction performances of various order selection criteria, for all classes of the parametric models, are reported in Table 1. Specifically, median and the interquartile range (IQR) of RMSE are reported for different prediction horizons (PH).

Besides considering patient-specific model complexity, achieved by individualizing the model order with AIC, BIC or CV, in Table 1 we also considered the use of population order (PopOrd) for all patients: the model complexity is not individualized while the model parameters are individual specific. This option accelerates model identification in a subject by removing the model-order selection step.

No significant differences between the considered complexity methods are found. This is in line with results that compared the same degrees of freedom using simulated data. In view of this, we decided to use a population order (PopOrd) for the remainder of the analysis. Table 1 shows also the median and IQR of the selected orders: BIC selected the lowest orders, as expected being BIC one of the most conservative parsimony criterion; CV selected the highest orders. Population orders (PopOrd) provides a trade-off between these two ends.

TABLE 1

Comparison of complexity criteria for different parametric approaches. Median [IQR] prediction performance as RMSE [mg/dL] for different prediction horizons, associated with respective p-values, along with the median [IQR] of the selected orders

| [min] | 30 | 60 | 90 | 120 | Order |
|---|---|---|---|---|---|
| a) ARX | | | | | |
| PopOrd | 18.2 [2.9] | 31.4 [5.6] | 39.6 [5.5] | 44.2 [5.4] | 13 |
| CV | 18.2 [2.9] | 31.3 [5.5] | 39.7 [5] | 43.9 [5.1] | 18 [5.5] |
| BIC | 18.4 [3] | 30.9 [6.5] | 40.4 [4.5] | 45.0 [5.5] | 4 [1] |
| AIC | 18.1 [3] | 31.1 [5.4] | 39.9 [4.9] | 43.9 [4.8] | 8 [11] |
| p-value | 0.98 | 0.98 | 0.95 | 0.96 | |
| b) ARMAX | | | | | |
| PopOrd | 18.1 [3.2] | 31.2 [6.7] | 39.3 [6.4] | 43.5 [9.1] | 11 |
| CV | 18.5 [3] | 31.8 [6.4] | 40.0 [5.4] | 43.1 [7.6] | 18 [4] |
| BIC | 18.2 [2.9] | 30.9 [6] | 39.3 [5.4] | 43.5 [5.5] | 2 [1] |
| AIC | 18.4 [4.4] | 30.9 [7.1] | 40.4 [5.4] | 43.6 [8] | 4 [6] |
| p-value | 0.85 | 0.97 | 0.99 | 0.99 | |
| c) ARIMAX | | | | | |
| PopOrd | 18.3 [2.4] | 31.8 [5.5] | 40.3 [3.3] | 46.4 [3.8] | 11 |
| CV | 18.6 [3] | 31.9 [6.5] | 41.4 [5.5] | 45.2 [6.5] | 18 [7] |
| BIC | 18.8 [3.6] | 34.1 [7.7] | 43.8 [9.4] | 50.4 [11.5] | 1 [3] |
| AIC | 18.3 [2.5] | 31.5 [5.7] | 40.5 [4.7] | 44.0 [4.5] | 6 [6] |
| p-value | 0.82 | 0.55 | 0.19 | 0.07 | |
| d) BJ | | | | | |
| PopOrd | 18.5 [3] | 30.7 [5.9] | 38.1 [5.9] | 42.7 [7.5] | 7 |
| CV | 18.0 [5.2] | 30.8 [8.9] | 40.5 [7.7] | 42.7 [8] | 13 [2.5] |
| BIC | 18.5 [3.2] | 31.0 [6.1] | 39.8 [5.7] | 43.0 [5] | 2 [0] |
| AIC | 18.4 [3.3] | 31.0 [6.5] | 39.1 [5.8] | 43.1 [5.7] | 4 [3.5] |
| p-value | 0.99 | 0.99 | 0.99 | 0.99 | |

Table II reports the prediction performance of all considered models for a 60-min ahead prediction horizon. All the considerations drawn in this case remain valid for other prediction horizons presented in Table IV. For baseline comparison, besides individualized models obtained with parametric and non-parametric approaches, we also report the performance of population models, i.e., universal models identified on the data of all subjects, with parametric and non-parametric approaches.

TABLE II

| | MODEL TYPE | | | | | |
|---|---|---|---|---|---|---|
| CLASS | RMSE [mg/dL] | COD [%] | | TG [min] | | |
| PARAMETRIC | POPULATION | | ARX | 35.5 [7.6] | 51.5 [12.7] | 15 [5] |
| | | | ARMAX | 34.9 [7.8] | 52.3 [12.6] | 15 [4] |
| | | | ARIMAX | 35.9 [7.9] | 50.2 [13] | 10 [4] |
| | | | BJ | 34.1 [8.8] | 53 [16.8] | 20 [5] |
| | INDIVIDUALIZED | PEM | ARX | 31.4 [5.6] | 55.7 [13.1] | 15 [9] |
| | | | ARMAX | 31.2 [6.7] | 53.5 [10.4] | 15 [5] |
| | | | ARIMAX | 31.8 [5.5] | 51.6 [19.3] | 10 [5] |
| | | | BJ | 31.7 [5.9] | 55.4 [20.2] | 20 [9] |
| | | PH-step | ARX | 33.9 [7.2] | 54.6 [8.7] | 15 [13] |
| | | | ARMAX | 34.8 [7.2] | 52.5 [16.4] | 20 [10] |
| | | | ARIMAX | 34.8 [8.5] | 51.8 [13.6] | 15 [10] |
| | | | BJ | 36.1 [6.8] | 41.1 [39.9] | 15 [9] |
| NON-PARAMETRIC | POPULATION | | Matlab | 32.0 [5.3] | 52.3 [17.6] | 15 [4] |
| | | | Ad-hoc implementation | 31.4 [5.5] | 52.6 [16.6] | 15 [5] |
| | INDIVIDUALIZED | | Matlab | 31.7 [4.7] | 53.2 [15.9] | 20 [10] |
| | | | Ad-hoc implementation | 29.8 [5.9] | 57.4 [12] | 20 [9] |

The first thing shown by Table II is that parametric population predictors are systematically outperformed by their individualized counterparts: the best median RMSE achieved by population models is about 34.1 mg/dL, while for individualized models RMSE is always lower than 32 mg/dL. This confirms that inter-patient variability impacts severely on population models' efficacy.

Comparing the parametric models with respect to the parameter estimation method, we can see that the predictors identified by minimizing the 60-min prediction error achieve similar or slightly worse performance compared to models selected with PEM. This is in line with the theory stating that PEM is optimal in a suitable statistical sense.

Regarding model class, the last degree of freedom of the parametric approaches, no significant difference can be found in RMSE or COD between ARX, ARMAX, ARIMAX, or BJ, in line with results previously obtained. Nonetheless, BJ provides superior TG, median of 20 min, with respect to the other model classes.

Finally, Table II shows that the best prediction performance is achieved by the non-parametric approach, in particular by the ad-hoc implementation achieving a median RMSE of about 29.8 mg/dL and a median COD of about 57.4%. This implementation slightly outperforms the Matlab standard function. The improvement is achieved while providing the same time gain (median TG=20 min) offered by BJ models, the most effective among the parametric models. This conclusion if further supported by FIGS. 5*a*-5*d*, which compare a parametric model (specifically BJ) to a non-parametric one (ad-hoc implementation). The upper panel of the figures report the boxplots of COD achieved by the two methods in the population for PH=30, 60, 90, and 120 min. Non-parametric models provide an improvement of COD of about 2%, 7%, 21%, and 41% for, respectively, a PH=30, 60, 90, and 120 min. The bottom panel of each figure reports the ΔCOD, that is the difference between COD achieved by the non-parametric model in one patient minus the COD of the parametric model derived for the same patient. Notably, these plots show that the difference is positive in a large majority of the subjects, meaning the prediction improvement is achieved not only in average but in most of the subjects. A paired-sample t-test confirms that the prediction accuracy is significantly different for PH=30, 60, and 90 min (p-value≤0.001, p-value=0.003 and p-value=0.03 respectively), while for PH=120 min, p-value=0.07.

TABLE III

| | | MODEL | PH [min] | | | |
|---|---|---|---|---|---|---|
| MODEL | TYPE | CLASS | 30 | 60 | 90 | 120 |
| LINEAR | POPULATION | Parametric | 23.7 [5.6] | 34.1 [8.8] | 42.3 [11.8] | 49.1 [11.3] |
| | | NonParametric | 18.8 [3] | 31.4 [5.5] | 40.1 [9.6] | 47.2 [9.3] |

TABLE III-continued

| MODEL | TYPE | MODEL CLASS | PH [min] 30 | 60 | 90 | 120 |
|---|---|---|---|---|---|---|
| | INDIVIDUALIZED | Parametric | 18.5 [3] | 31.7 [5.9] | 38.7 [5.9] | 49.3 [8.2] |
| | | NonParametric | 17.5 [2.7] | 29.8 [5.9] | 38.1 [4.5] | 46.6 [8.3] |
| NON-LINEAR | POPULATION | LSTM | 19.4 [3.2] | 32.9 [5.8] | 41.3 [5.7] | 47.6 [7.4] |
| | | GRU | 19.2 [2.3] | 31.2 [5.9] | 41.7 [5.9] | 48.1 [8.9] |
| | | TCN | 18 [1.6] | 31.9 [5.9] | 39.4 [6.7] | 47.5 [8.6] |
| | INDIVIDUALIZED | LSTM | 24.1 [7.1] | 36.2 [7.3] | 42.7 [5.2] | 49.2 [5.8] |
| | | GRU | 20.2 [4.6] | 33.1 [9.0] | 40.6 [6.4] | 48.9 [6.6] |
| | | TCN | 20.2 [3.5] | 35.5 [7.1] | 45.1 [6.4] | 49.0 [7.6] |

In some aspects the systems and techniques described herein concern the derivation of a patient-specific model of the glucose-insulin interaction for personalized glucose predictions and personalized automated glucose control. Given this, we focused on a systematic analysis of linear data-driven model-learning techniques, since linear approaches have a number of advantages previously discussed for prediction and control. Nonetheless, the patient physiology is nonlinear: therefore, one might wonder if resorting to non-linear data-driven approaches has the potential to significantly improve glucose prediction. As a preliminary investigation of this question, we implemented three state-of-art deep-learning (DL) architectures producing non-linear models. The objective of this analysis is not an exhaustive exploration of these techniques and of the associated degrees of freedom, but only to find whether they provide drastically different performances as compared to the techniques considered in this work, using the same amount of data. In particular, we considered two different recurrent neural network (RNN) architectures, that implement feedback connections in order to capture temporal dependencies in sequential data: a long-short term memory (LSTM), and a gated recurring unit (GRU). Furthermore, we implemented a temporal convolutional network (TCN), that, compared to RNN, uses convolution operations helping in capturing local information along with temporal information. As for the linear techniques, DL methods were used both to derive a population model, identified using all the available data, and to learn a patient-specific model, using only data of a specific subject. Table III presents a comparison of the achieved performance, in terms of RMSE for different PHs.

In comparison to linear strategies, non-linear DL techniques achieve better performance using a population model, probably because they need a larger dataset to accurately estimate their parameters. Furthermore, their structure is highly flexible, so that it is likely that they will internally handle inter-patient variability to a certain extent. Nonetheless, none of these DL approaches drastically outperform linear models, and they actually achieve slightly inferior performance for each PH with respect to the proposed linear non-parametric technique. This preliminary analysis does not exclude the possibility that other DL or non-linear machine-learning algorithms might outperform the linear black-box technique proposed, but it shows that the linear assumption is a viable alternative to more complex models.

With respect to other (linear and non-linear) methods, our findings, in terms of prediction accuracy, are comparable or slightly better. However, a word of caution is due: a comparison of literature works based on numerical results only could be misleading, due to the use of different datasets, pre-processing techniques and evaluation metrics.

A different version of the non-parametric approach was tested using Gaussian processes or kernel-based adaptive filters, obtaining results aligned with our findings. Nonetheless, the Stable-Spline kernel used herein is specifically designed to enforce stability of the predictor's impulse response, an important feature for control purposes.

To avoid the need of gathering simultaneously and synchronously glucose, insulin and meal data, a number of contributions in the literature tried to avoid the use of any additional signals, employing different system identification, ML or DL approaches using CGM-only data. However, the use of these further signals has been shown to enhance prediction performance, and this finding has also been verified in this work. In particular, in FIGS. 6*a* and 6*b* we compare the performance achieved by a CGM-only model, a parametric model identified using insulin and meal and a non-parametric model with inputs. Median values over the population of the prediction's COD and RMSE as a function of PH are reported, respectively, in FIGS. 6*a* and 6*b*. As anticipated, including inputs improves the prediction's accuracy, in particular for a PH greater than 45 min.

In this work, we showed that personalized models provide an effective tool to handle variability among subjects (inter-patient variability). These personalized models should also be kept updated to follow the changes over time occurring to the patient physiology (intra-patient variability). To accomplish this, a number of contributions in the literature effectively employed recursive approaches that update the model each time new data arrive (e.g., every 5 min).

While this is a well-established procedure for on-line model-adaptation, in the specific application less frequent model updates are sufficient to track the slow changes in patient dynamics. In view of this, we envision daily or weekly model updates achieved by running off-line the identification procedure on patient data collected in the past. This periodically-repeated batch model-identification can be performed using the algorithm investigated in this work as they are, without the need of modification to make them recursive.

A final comment on the technological architecture of a system running the proposed algorithms. Artificial Pancreas systems and advanced decision support systems that could benefit from personalized models are implemented on devices capable of obtaining CGM, meal and insulin data, offering effective Graphical User Interfaces and suited to host (possibly advanced) algorithms thanks to their significant computational power. An example of such device is the Diabetes Assistant (DiAs), a smartphone-based platform previously mentioned in this work and adopted in several closed-loop trails. These systems also stream data to remote servers, to allow patient telemonitoring. The batch model-updates investigated in this paper could be performed on the abovementioned devices or moved on the remote servers storing patient data, thus alleviating the local computational burden. Personalized and periodically updated models are the natural way to handle the large intra- and inter-subject variability in diabetes. They can be used to create accurate patient-specific predictor of future glucose levels and to design personalized control algorithms for more effective AP systems.

In summary, aspects of the systems and techniques described herein focused on linear data-driven techniques, using insulin and meal information together with CGM data. Both parametric and non-parametric approaches, with the associated degrees of freedom, were systematically explored. To reduce the problem of collinearity of inputs, a specific input transformation was applied to the inputs.

Results showed that personalized models outperform their population counterparts, thus proving the importance of handling inter-subject variability. Moreover, we showed that the non-parametric approach allows to obtain models consistently more effective over the subjects, with a relative improvement that increases as the prediction horizon increases. A preliminary comparison showed that non-linear data-driven techniques based on deep-learning architecture do not outperform linear model accuracy. Results confirmed that adding further information, such as CHO and injected insulin, provides a practically relevant improvement of prediction accuracy for PH greater than 45 min.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general-purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on non-transitory computer-readable medium. By way of example, and not a limitation, such non-transitory computer-readable media can comprise RAM, ROM, EEPROM, CD-ROM or other optical disk storage, magnetic disk storage or other magnetic storage devices.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as and/of unless expressly stated otherwise. Similarly, a group of items linked with the conjunction 'or' should not be read as requiring mutual exclusivity among that group, but rather should be read as 'and/or' unless expressly stated otherwise.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

TABLE IV

Performance metrics (median [iqr] among patients) of all identified models. for PH = 30, 90, and 120 min

| MODEL | TYPE | | MODEL Class | PH = 30 min RMSE [mg/dL] | PH = 30 min COD [%] | PH = 30 min TG [min] | PH = 90 min RMSE [mg/dL] | PH = 90 min COD [%] | PH = 90 min TG [min] | PH = 120 min RMSE [mg/dL] | PH = 120 min COD [%] | PH = 120 min TG [min] |
|---|---|---|---|---|---|---|---|---|---|---|---|---|
| PARAMETRIC | POPULATION | | ARX | 22.2 | 80.3 | 10 | 44.2 | 26 | 15 | 50.2 | 2.6 | 15 |
| | | | | [5.1] | [7.1] | [4] | [11] | [11.9] | [5] | [9.4] | [12.1] | [9] |
| | | | ARMAX | 21.9 | 80.9 | 10 | 42.6 | 28.8 | 20 | 51.5 | 1.6 | 15 |
| | | | | [5.1] | [6.9] | [0] | [10.5] | [14] | [5] | [9.4] | [9.1] | [5] |
| | | | ARIMAX | 22.4 | 80.1 | 10 | 45 | 20.5 | 20 | 51.3 | −3.6 | 10 |
| | | | | [5.3] | [7.3] | [5] | [10.2] | [15.8] | [0] | [9.1] | [15.6] | [5] |
| | | | BJ | 23.7 | 79.2 | 10 | 42.3 | 27.1 | 25 | 9.1 | 7.8 | 10 |
| | | | | [5.6] | [8] | [0] | [11.8] | [19.3] | [10] | [11.3] | [20.8] | [19] |
| | INDIV. | PEM | ARX | 18.2 | 84.9 | 10 | 39.6 | 27 | 15 | 48.1 | 6.1 | 20 |
| | | | | [2.9] | [6.2] | [5] | [5.5] | [19.9] | [10] | [9.6] | [14.5] | [24] |
| | | | ARMAX | 18.1 | 84.6 | 10 | 39.3 | 26.3 | 20 | 49 | −1.2 | 35 |
| | | | | [3.2] | [5.8] | [4] | [6.4] | [14.5] | [9] | [10.1] | [27.9] | [80] |
| | | | ARIMAX | 18.3 | 84.7 | 10 | 40.3 | 24.5 | 10 | 47.5 | −0.1 | 10 |
| | | | | [2.4] | [7.9] | [0] | [3.3] | [17.8] | [15] | [10.9] | [21.9] | [96] |
| | | | BJ | 18.5 | 84.9 | 10 | 38.7 | 29 | 25 | 49.3 | 1.6 | 50 |
| | | | | [3] | [7.4] | [4] | [5.9] | [26.2] | [20] | [8.2] | [21.8] | [99] |
| | | PH-step | ARX | 20.1 | 82.5 | 10 | 42.7 | 28.3 | 20 | 48.1 | 3 | 35 |
| | | | | [3.4] | [4.2] | [0] | [8.3] | [15] | [15] | [8.4] | [19.1] | [31] |
| | | | ARMAX | 21.8 | 82.1 | 10 | 45.3 | 27 | 25 | 52.1 | 0.2 | 20 |
| | | | | [3.7] | [5.3] | [0] | [8.3] | [24.3] | [19] | [8.4] | [39.3] | [28] |
| | | | ARIMAX | 21.3 | 81.9 | 10 | 43.7 | 22.6 | 20 | 52.1 | −0.5 | 10 |
| | | | | [3.7] | [4.9] | [4] | [8.4] | [19.2] | [15] | [7.2] | [25.8] | [60] |
| | | | BJ | 21.4 | 79.3 | 10 | 45.7 | 4.9 | 15 | 55.6 | −17.9 | 10 |
| | | | | [4.4] | [4.7] | [0] | [4.2] | [56.6] | [14] | [15.4] | [87.2] | [13] |
| NON PARAMETRIC | POPULATION | | Matlab ® | 18.9 | 82.6 | 10 | 39.9 | 29.9 | 15 | 47.3 | 6.7 | 25 |
| | | | | [2.5] | [8.8] | [4] | [9.3] | [16.9] | [9] | [8.9] | [15.6] | [63] |
| | | | Ad-hoc implentation | 18.8 | 82.5 | 10 | 40.1 | 26.9 | 15 | 47.2 | 6.2 | 25 |
| | | | | [3] | [8.3] | [4] | [9.6] | [14.8] | [5] | [9.3] | [13.8] | [38] |
| | INDIV. | | Matlab ® | 18.6 | 83.4 | 10 | 40.3 | 25 | 25 | 47.5 | 9.6 | 30 |
| | | | | [2.4] | [5.4] | [5] | [4.5] | [27.7] | [18] | [9.2] | [21.2] | [63] |
| | | | Ad-hoc implentation | 17.25 | 85.9 | 10 | 38.1 | 31.8 | 20 | 46.6 | 10.3 | 20 |
| | | | | [2.7] | [5.8] | [5] | [4.5] | [11.5] | [14] | [8.3] | [17] | [61] |

The invention claimed is:

1. A computer-based method of predicting future blood glucose concentrations of an individual patient, comprising:

receiving data sets for the individual patient including previous glucose levels over time for the individual patient, meal intake data over time for the individual patient, and exogenous insulin delivered to the individual patient over time;

pre-processing the meal intake data and the exogenous insulin data including:

transforming a meal intake signal by subtracting a sample mean of the meal intake signal, and transforming an exogenous insulin signal by subtracting a basal insulin amount and a meal-centric bolus term, the meal-centric bolus term being based on an insulin-to-carbohydrate ratio (ICR) of the individual patient;

estimating a plurality of impulse response functions based on the data sets for the individual patient to generate a personalized model for the individual patient, the impulse response functions being functions of a kernel; and applying a linear predicting technique to the personalized model for the individual patient based on the estimated plurality of impulse response functions to obtain a predicted blood glucose concentration of the individual patient at a future time.

2. The computer-based method of claim 1, wherein the personalized model for the individual patient is based on a time-invariant model.

3. The computer-based method of claim 1, wherein the previous glucose levels over time for the individual patient are provided by a continuous glucose monitor.

4. The computer-based method of claim 1, wherein the kernel is a Reproducing Kernel Hilbert Space (RKHS).

5. The computer-based method of claim 4, further comprising estimating kernel hyperparameters using maximum marginal likelihood or cross-validation.

6. The computer-based method of claim 1, wherein the plurality of impulse response functions are estimated using a nonparametric estimation technique.

7. The computer-based method of claim 6, wherein the nonparametric estimation technique comprises a support vector regression, a Gaussian regression, and a Tikhonov regularization.

8. The computer-based method of claim 1, wherein estimating the plurality of impulse response functions to generate the personalized model for the individual patient are performed by a server.

9. The computer-based method of claim 8, further comprising:

receiving, over a wireless network, glucose data from a continuous glucose monitor worn by the individual patient, wherein receiving the glucose data from a continuous glucose monitor and applying the linear predicting technique to obtain the predicted blood glucose concentration of the individual patient at a future time are performed by a smartphone.

10. The computer-based method of claim 9, further comprising sending, by the smartphone over the wireless network, the predicted blood glucose concentration of the individual patient at a future time to an automated insulin delivery system coupled to the individual patient.

11. The computer-based method of claim 10, wherein the wireless network comprises a low energy Bluetooth connection between the smartphone and the continuous glucose monitor, and a low energy Bluetooth connection between the smartphone and the automated insulin delivery system.

* * * * *